United States Patent [19]
Larson

[11] Patent Number: 6,066,129
[45] Date of Patent: May 23, 2000

[54] MEDICAL LASER CONTROL SYSTEM

[76] Inventor: Dean W. Larson, 15 Carrotwood Ct., Fort Myers, Fla. 33919

[21] Appl. No.: 09/015,639

[22] Filed: Jan. 29, 1998

[51] Int. Cl.$^7$ .................................................. A61B 17/36
[52] U.S. Cl. .............................................. 606/10; 606/16
[58] Field of Search ................... 606/1, 2, 9, 10, 606/11, 12, 13, 14, 15, 16, 17, 19, 46, 51

[56] References Cited

U.S. PATENT DOCUMENTS

| | | | |
|---|---|---|---|
| 4,657,018 | 4/1987 | Hakky | 606/46 |
| 4,781,185 | 11/1988 | Kauphusman et al. | 606/2 |
| 5,150,704 | 9/1992 | Tatebayashi et al. | 606/19 |
| 5,480,409 | 1/1996 | Riza | 606/51 |
| 5,628,744 | 5/1997 | Coleman et al. | 606/12 |
| 5,653,706 | 8/1997 | Zavislan et al. | 606/9 |
| 5,662,644 | 9/1997 | Swor | 606/9 |
| 5,788,688 | 8/1998 | Bauer et al. | 606/1 |
| 5,843,072 | 12/1998 | Furumoto et al. | 606/9 |

Primary Examiner—Linda C. M. Dvorak
Assistant Examiner—Sonya Harris-Ogugua
Attorney, Agent, or Firm—Pendorf & Cutliff

[57] ABSTRACT

A medical laser adapted to be controlled remotely from the main operating console, and more particularly, a handpiece held by the surgeon which includes one or more remote controls for actuating and controlling the operation of a medical laser.

18 Claims, 7 Drawing Sheets

Fig. 3

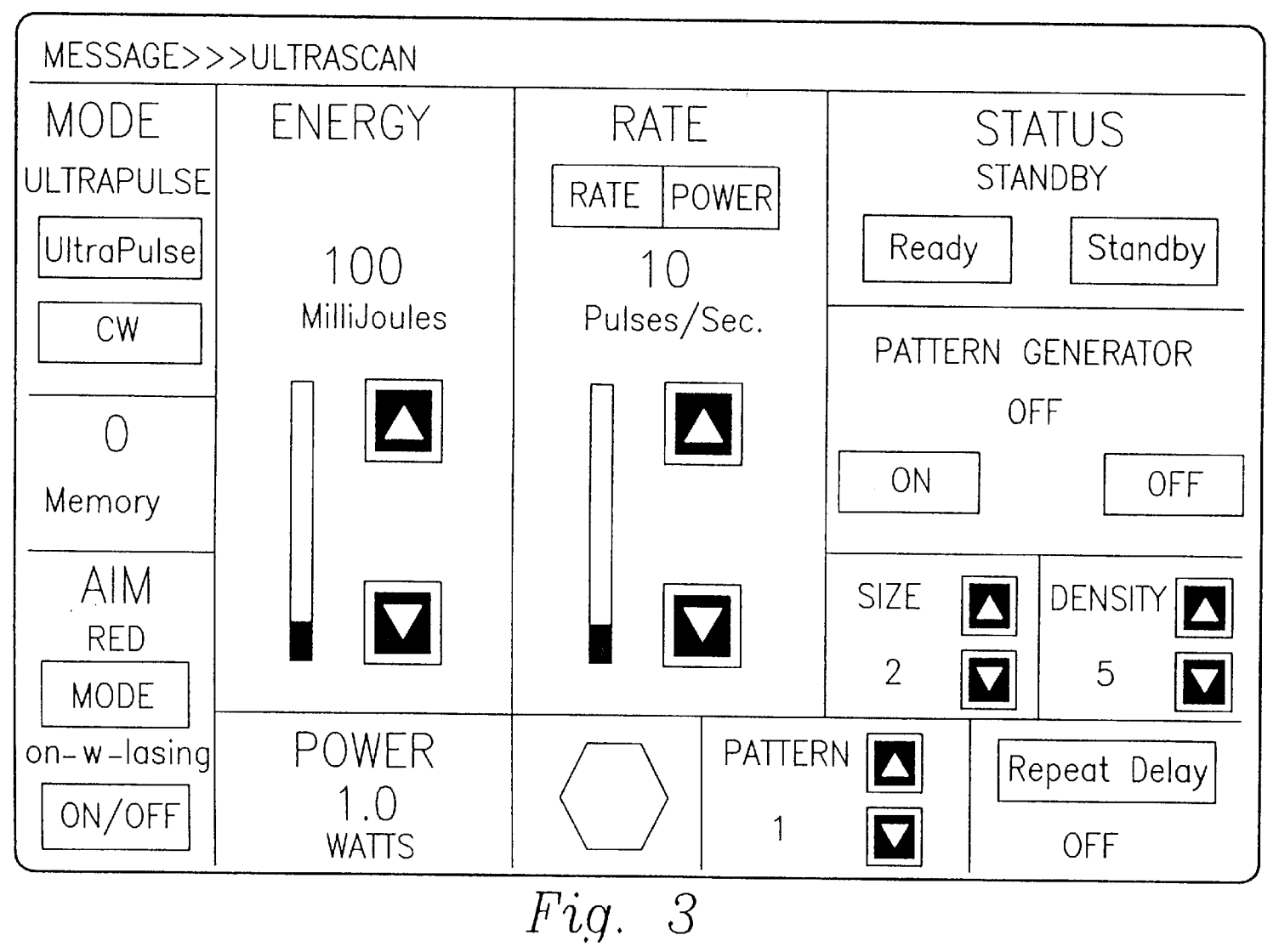

MESSAGE>>>ULTRASCAN

MODE
ULTRAPULSE
[UltraPulse] [CW]
0
Memory

AIM
RED
[MODE]
on-w-lasing
[ON/OFF]

ENERGY
100
MilliJoules
◀ ▶

POWER
1.0
WATTS

RATE
[RATE] [POWER]
10
Pulses/Sec.
◀ ▶

STATUS
STANDBY
[Ready] [Standby]

PATTERN GENERATOR
OFF
[ON] [OFF]

SIZE ◀ ▶   DENSITY ◀ ▶
2            5

PATTERN ◀ ▶
1

[Repeat Delay]
OFF

MEDICAL LASER CONTROL SYSTEM

BACKGROUND OF THE INVENTION

1. Field of the Invention

The invention concerns a medical laser adapted to be controlled remotely from the main operating console, and more particularly, a handpiece held by the surgeon which includes one or more remote controls for actuating and controlling the operation of a medical laser.

2. Description of the Related Art

Medical lasers were first used in ophthalmology for diabetic retinophthalmology. In this procedure the ophthalmologist uses one hand to hold a lens on the patients eye and the other hand to work a slip lamp. Since both hands are occupied, the laser system is activated via a switch built into a foot pedal.

Even today, medical lasers as used in dermatologic and reconstructive and plastic procedures are activated by foot pedals. Examples of foot pedal systems for controlling medical lasers and surgical implements can be found in U.S. Pat. No. 4,862,886 (Clarke et al.) teaching a laser therapy system for laser angioplasty wherein an excimer laser having a coherent beam of ultraviolet radiation is operated via a foot pedal; U.S. Pat. No. 5,568,859 (Levy et al.), directed to a compact sized foot switch for control of medical laser surgery systems; U.S. Pat. No. 5,554,894 (Sepielli) teaching a complex footswitch for ophthalmic surgery including a rotatable foot pedal, a spring member which biases the foot pedal to resist rotation and an adjustment mechanism for adjusting the bias of the spring member to a surgeon selected value; U.S. Pat. No. 5,166,513 teaching a dual actuation photoelectric foot switch for a medical laser; and U.S. Pat. No. 5,580,347 (Reimels) teaching a system for performing surgery on a patient's eye including a handpiece, a control module, and a foot pedal, with processing circuitry located in the foot pedal rather than in the control module.

As demonstrated by these patents, the conventional thinking in this industry is that medical instruments, and particularly medical lasers, are to be activated via a foot pedal.

Cosmetic laser surgery has advanced significantly in recent years. In early laser systems a surgeon performed skin ablation by activating a foot pedal one time each time he desired to fire a laser to treat one small area or "spot". After treating one spot the surgeon repositioned the laser to lay down the next spot perfectly positioned beside the previous spot. An experienced surgeon could lay down as many as three spots per second, evenly spaced and not overlapping. Thousands of spots may be required to give skin an even treatment.

The development of the computer pattern generator (CPG) revolutionized the speed and control of laser surgery. This device attaches to the distal end of a laser articulated arm and is contained within a plastic housing or handpiece held in the hand(s) of the surgeon. As the laser beam goes through the articulated arm and passes through the CPG it is reflected by a tiny mirror controlled by a computer. The mirror aims the laser beam so that it can lay down patterns of spots, for example 81 spots in a 9×9 square pattern in a half a second. Every time the foot pedal is activated, the surgeon can lay down 81 spots in a perfect pattern. Then, all the surgeon needs to do is line up the next square beside the previous square, activate the laser, and hold the CPG steady as it fires and lays down each successive pattern of 81 spots.

The CPG can lay down not only a square pattern, but can be programmed to lay down, e.g., a single spot, a row of spots, two rows of spots, a triangle pattern, a circular pattern, etc. Thus, if during the course of a surgical procedure the surgeon notices that he skipped a narrow strip of skin, he may stop laying down broad 9 by 9 square patterns and reprogram the CPG to lay down a 1 by 9 pattern or a 2 by 9 strip pattern to fill in the missed strip. However, in practice, a surgeon will develop a rhythm. This is important, since skin will heat up when being lased, and the temperature of skin influences the rate of ablation. A rhythmic treatment of skin will ensure even heating of adjacent skin. It is difficult for a surgeon to interrupt the flow of the procedure for the amount of time it takes to reprogram the CPG to change the pattern to a 1 by 9.

Instead of reprogramming the CPG, surgeons tend to develop a feel for the foot pedal control of the CPG, and find that it is possible to depress the foot pedal for only a very short fraction of the time needed to generate the full pattern. The surgeon will thus leave the CPG set to generate a 9 by 9 pattern but interrupt the laser activation as soon as the laser laid down the first 1 by 9 or a 2 by 9 pattern.

While it may be possible for a surgeon with fast foot control to limit the CPG to laying down one or two rows of spots, it is nearly impossible to control a CPG to lay down only a single spot. Thus, some reprogramming of the CPG during some time in the procedure will inevitably be necessary.

The laser system can be programmed to select for various pattern sizes, pattern shapes (some systems having 79 preprogrammed patterns, energy, power, pulse or continuous wave, and pulse rate. Further, as a safety feature, and so that the laser is not left energized unnecessarily, the laser system is switchable between a "ready" mode and a "standby" mode. Since the surgeon is wielding the laser handpiece and is far from the control console, each change in setting requires the surgeon to request the console operator to enter the change of settings. Then, to verify that the desired settings were correctly entered, the surgeon must turn around, look at the display console or console mast display, then turn back to the patient and resume work. This tends to disrupt the flow of a surgical procedure.

As surgeons get accustomed to using the CPG, problems surface. One surgeon found that the CPG required her to stand all day on one foot, supporting all her weight on this foot, in order to be able to control the laser with her other foot. This surgeon suffered back pain because of the awkward position she was forced to stand in. Some surgeons perform this type of surgery 8 hours a day and for them this uncomfortable posture becomes a real problem. It is of course possible to perform the surgery while sitting, but for ergonomic reasons it becomes more awkward to use the foot to control the laser; thus, standing is the conventional position for the surgeon.

Another problem with the existing system is that the foot pedal and foot pedal cord are always in the way. Many surgeons find the foot pedal cord to be a serious inconvenience. If the surgeon begins a cosmetic procedure on one side of a patient's face and wants to move to the other side of the patient, he must reposition the foot pedal and cord. This tends to be such a hassle that surgeons instead lean over the patient to work on the other side of the patient rather than moving the equipment, the foot pedal, and the foot pedal cord to the other side of the patient.

Yet another problem with the traditional foot pedal arrangement is that in the surgical theater, particularly in OB/GYN urology, the floor frequently becomes wet. Laser manuals warn the practitioner to discontinue use of the laser under such conditions, since the foot switch is liable to short circuit.

At least one company, Storz Instrument Company of St. Louis, Mo. (Storz), had recognized that there is, on the part of a number of surgeons, a desire to have a more "hands-on" control over the surgical equipment control systems they use. It was recognized that in, for example, a typical ophthalmic operation, a surgeon often has the assistance of a scrub nurse and a circulating nurse, and sometimes others. The surgeon spends much time peering through a binocular microscope to obtain a magnified view of the eye being operated upon. Thus, the surgeon typically requests assistance from the nursing staff for activity such as changing pressures, power levels, and cut rates, raising or lowering the IV bottle containing the saline solution used to irrigate the eye, and changing the control modes of the equipment. Under some circumstances, such as a cataract operation where an emergency vitrectomy must be performed, the surgeon may well be involved in completing one task, such as a phacoemulsification procedure, while the other members of the surgical team are busy setting up for a different surgical procedure, such as a vitrectomy. Storz recognized that it would be extremely useful if the surgeon could be provided with a remote control console for controlling the surgical equipment, particularly one which could provide most of the functionality of the main control console.

Such a remote console is in fact disclosed in U.S. Pat. No. 5,249,121 (Baum et al). However, even though this patent teaches in great depth how to provide a remote console for changing settings on a main console, it continues to use a foot pedal control to operate surgical instruments. Further, there is no mention of a medical laser system.

Another problem, briefly alluded to above, is the problem of providing the surgeon with laser system status information during surgery. Conventional displays include LCD, LED, video and/or CRT displays mounted on a console which is usually behind the back of the surgeon during surgery. To view the data appearing on the display for purposes of changing settings, the surgeon must take his eyes of the patient, loose rhythm and concentration, turn around to read the display, order changes in settings, turn back to the patient, then return to the display to confirm entry of the correct settings, and turn back to patient. Furthermore, the loupe worn by the surgeon can make it more difficult for him to turn and view the console. Also, a surgeon commonly becomes preoccupied with the current task, and he may simply forget to constantly review the important safety data provided on the display.

There is thus a need for an improvement in the laser control system which overcomes the above problems, and it is an object of the present invention to provide such improvements.

SUMMARY OF THE INVENTION

In a first aspect, the present invention provides a remote laser actuator which replaces the foot pedal and is provided directly on the handpiece held by the surgeon. This modification provides a greater feeling of control over the laser, increases speed and accuracy, and eliminates the problems of having to reposition the foot pedal cord and tripping over the foot pedal cord.

In a second aspect, the present invention provides a remote controller which simulates one or more of the functionalities provided through the operator interface on a main laser system control console. The remote console should comprise: communication means, connected to the main processor, for causing the remote console to communicate with the control system; and display means, connected to the communication means, for simulating the display of at least part of the information associated with the laser system. The communication means may comprise a serial communications interface and interrupt generation means. The remote console may include a microcontroller and a plurality of light emitting means and/or liquid crystal displays.

In a further aspect of the invention there is provided a remote control console, either on a separate panel or, more preferably, directly on or incorporated in the CPG handpiece, having a display region capable of displaying or illuminating a variety of different indications and messages depending upon the particular surgical laser procedure being performed.

It is a further aspect of the invention to provide a plurality of input switches disposed adjacent such a display region on the remote unit for allowing a user to select different surgical procedures or adjust various controls, and/or parameter settings as desired.

The present invention runs contrary to the conventional practice of setting up a laser for two man operation, a surgeon to aim the laser and a control console operator to adjust the parameters of the laser system. Surprisingly, when tested under conditions of actual use, it was found that the benefits of having full control of the laser and CPG in the hands of the surgeon improved the speed and control of the surgical procedure and eliminated any possibility of miscommunication between the surgeon and console operator.

Further, the elimination of the foot pedal eliminated one of the main hassles associated with what, after the present invention, can be referred to as the outdated foot pedal laser control system. The surgeon can now focus his attention on the surgical procedure rather than sending constant instructions to the console operator and checking the laser system display to see if his instructions are carried out. The surgeon is more comfortable since he can sit or stand on two feet without having to operate a foot pedal. The surgeon can quickly reprograms the CPG when necessary to fire one spot or one row of spots rather than rely on foot control to try to interrupt the 81 dot pattern on which the CPG is set. The surgeon has control of the laser in the handpiece guiding the laser CPG, a more natural feel than controlling the laser via the foot pedal. As a result, the surgical procedure is completed with greater precision in much less time.

The present invention further provides a surgeon's laser control information system including a microcontroller programmed to perform a plurality of tasks. Upon power-up, the system displays a sequence of selections that allow the surgeon to see the present settings and to select any value for a specific laser parameter, so that the surgeon knows the status of the laser and can safely perform his surgery.

As an additional feature, an embodiment of the present invention includes a non-volatile static RAM that maintains the data stored within it even after a long period of power interruption. The preferred embodiment periodically stores all current settings and warnings in this non-volatile RAM so that a profile of the entire surgical procedure can be maintained for later use, by downloading to an external computer.

Furthermore, the present invention optionally provides a display, wholly within the surgeon's protective eyewear or loupe, so that he can easily monitor pertinent laser status information provided from the microcontroller, such as power, ready/standby status, pattern, etc. In one embodiment the display includes a series of LED digits in the upper or lower portion of the protective eye wear, a reflective surface on the upper portion, and a partially reflecting surfaces on the transparent optics of the eyewear or loupe. Thus, after reflection, the optical path from the LEDs to the surgeon's eyes is sufficiently long that the surgeon can comfortably focus on the LED indications.

These and other features and advantages of the present invention will become more fully apparent from the following description and appended claims taken in conjunction with the accompanying drawings.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other laser actuation systems, remote control systems, and remote display systems for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the present invention reference should be made by the following detailed description taken in with the accompanying drawings in which:

FIG. 3 shows a typical control screen as presented at the console operator station.

DETAILED DESCRIPTION OF THE INVENTION

Figure 1:
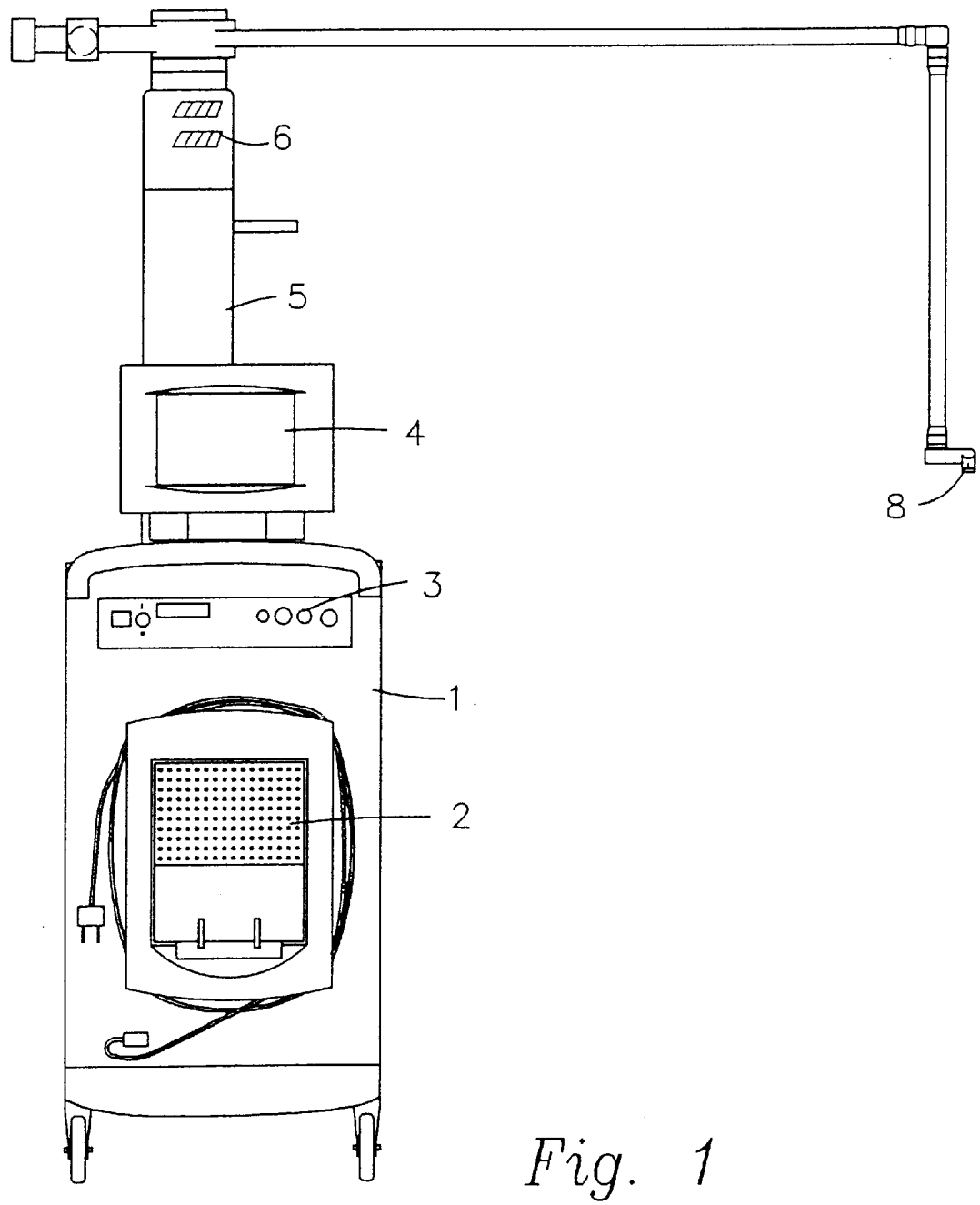
FIG. 1 shows a front view of a medical laser system with CPG and handpiece removed.

Having once conceived of the present invention, it was found that the basic optics and electronics necessary for construction of working embodiments were well within the skill of those working in this art. The remote activating switch and controls are most simply microswitches and membrane switches. Microswitches and membrane switches are well known in the art and need not be described herein. Microswitches are used where it is necessary to provide both an "on" signal and an "off" signal such as for activating and deactivating a laser. Membrane switches are used to send an "on" message and are used to change settings. For example, a "plus" membrane switch can be used to send a signal from the remote console to the main console to increase power, pattern number or pattern size, and a "minus" membrane switch can be used to send a signal to the main console to decrease power, pattern number or pattern size. Communication between the remote console and the main console can be by means of multi-conductor cable, by cable via microprocessor, by infrared link, or by radio frequency link as is well known in the art and as discussed in greater detail below.

The settings of the laser are continuously displayed on the main operating console and one or more indications are repeated on the remote console or handpiece, or even in a heads-up display as discussed in greater detail below, such that both the surgeon and the operating console operator know at all times the selected instantaneous operating parameters of the laser system.

Turning first to the remote controls, in the present invention controls could be provided (a) directly on the surgeon's handpiece, (b) on a remote control panel with remote indicators as disclosed in U.S. Pat. No. 5,249,121, the disclosure of which is incorporated herein by reference, such that one or more remote control panels can be conveniently positioned around the patient, or (c) the more critical controls can be provided on the surgeon's handpiece, and less critical controls can be provided on remote control panels positioned around the patient.

The most important control element is the laser activation switch. This switch should always be provided on the surgeon's handpiece since it would be inconvenient for the surgeon to have to guide and position the laser handpiece with one hand and to have to look for the laser activation switch on the control panel and engage it with the other hand.

Accordingly, the present invention provides at least the laser activation switch directly on the laser handpiece, i.e., the CPG unit handpiece. With the laser operated by a microswitch provided on the CPG, the requirement for a foot pedal is completely eliminated, and the surgeon can stand comfortably on both feet or can sit without the sitting posture detracting in any way from his ability to control the laser. The feeling of control over the laser is greatly enhanced when the laser is operated by the fingertip control rather than by a foot pedal.

The laser activation switch is preferably a low profile (thin) microswitch provided at the distal (laser emitting) end of the handpiece, in the area in which the fingertips are normally located. Pressing the switch closes an "on" circuit and causes activation of the laser (as long as the laser is already in the "ready" mode), and releasing the switch causes the microswitch to flip back and close an "off" circuit, sending a deactivation signal to the laser. This allows the surgeon to operate the laser by simply pressing one finger down (laser on) and releasing the pressure (laser off). The microswitch may be connected to the main console via a three-wire electrical conductor or multi-conductor harness such as a flexible printed circuit. That is, the microswitch is connected to the operating console in the identical manner in which the foot pedal cord is connected to the main control console, the difference being that the fingertip switch control cord is routed along laser articulated arm to reach the fingertip microswitch rather than running along the floor to the foot pedal. The operating console is not changed and does not recognize whether the activation signal is being provided by a finger activated microswitch or a foot operated foot switch, the results being the same in either case.

The running of the cord along the articulated arm keeps the cord off the floor so that the problems of tripping over or running over the cord are eliminated. Further, since the electrical switch is no longer located on the floor, any potential problems associated with electrical shorts in the case that the floor becomes wet are eliminated. Further yet, since the trigger is now provided directly on the CPG handpiece, the trigger is always accessible to the surgeon even if the surgeon moves from one side of the patient to the other side; thus, the need to move a foot pedal whenever the surgeon moves has been eliminated.

As a safety feature, the microswitch for activation of the laser may also be provided with a "trigger guard", as found in hand guns but preferably made of plastic and running transverse rather than longitudinal to the axis of the laser. The trigger guard helps ensure that the laser can not be triggered inadvertently by bumping the CPG mounted laser activation microswitch against something, or by bumping anything against the microswitch.

In order to have important laser status information displayed to the surgeon so that the surgeon does not have to turn around and view the console mast or ask the main console operator for the laser status, a remote display is provided near the patient or, preferably, the CPG handpiece may be provided with one or more displays. In a very basic embodiment, the handpiece is provided only with a laser actuation microswitch and a small red LED placed on the handpiece where it is easily seen by the surgeon. More preferably, the handpiece is provided with a three-color LED wherein the three colors (e.g., red, green, and amber) indicate standby, ready, and laser firing, respectively. When the red LED is in the "off" condition it indicates that the laser is in the standby mode, and when the red LED is in the "on" or light emitting condition it indicates that the laser is in the ready mode. This LED indicator may be connected to the main control console via the same multiconductor wiring harness as provided for the microswitch. The selection and use of LEDs is well within the skill of those working in this art, and LEDs may be of the type disclosed in great detail in U.S. Pat. No. 5,621,225 (Shieh et al.) disclosing a method of fabricating a light emitting diode display package. This display package may be used to indicate not only "on-off", but may be used to display letters, numbers, or symbols, the method of pattern generation (on up to a 100×100 LED grid) being well described in this patent and being well known to those in this art. The display preferably includes a series of digits formed from combinations of LEDs (light emitting diodes), but may comprise an LCD display or any other type of display. Preferably, the display will be illuminated for ease of reading. The preferred embodiment comprises LEDs (which are inherently illuminating) and in other embodiments, an LCD display may be illuminated with a separate light source. Additional embodiments may provide a display of characters other than digits. Such characters may include symbols recognizable to a surgeon, for example, symbols signifying "laser malfunction". Flat screen video screens may also be used but this expensive technology tends to unnecessarily increase the price of the system and is thus not employed in the more basic systems according to the present invention.

In order to provide more convenience and to further improve the efficiency of the surgeon, it is preferred that one or more control switches (preferably including associated displays) are provided directly on the CPG handpiece in addition to the laser activation switch. These control switches and displays and electronics for communication with the main console may be the same as provided on the remote control panel in U.S. Pat. No. 5,249,121 discussed above, but any switches and displays may be used, and those characterized by being reliable, having low energy requirements, being compact and low weight, being easily manipulated while wearing surgical gloves, and having low profile (thickness) are particularly preferred.

It is of course possible, but not necessary, that the displays be provided in the form of a heads up display directly in the loupe or the protective eyewear worn by the surgeon. Methods of providing such a display are well known and need not be discussed in detail here. Reference may be made to simple systems such as the large multi-element LED as disclosed in U.S. Pat. No. 5,423,215 (Frankel) concerning a self-contained heads-up visual altimeter display for skydiving. However, it is difficult for the surgeon to change focus between the patient, who may be 18 inches or more from the surgeon, to the LED, which may be two inches from the eyes of the surgeon. Thus, for all but the most basic "on-off" indications which can be signaled by the on-off condition of a LED, the display is preferably placed at approximately the same focal distance from the eyes as the patient, which placement may be accomplished in a compact manner by use of mirrors as disclosed in U.S. Pat. No. 5,033,808 (Barr). Barr discloses a diver information system that displays information in the diver's line of sight without substantially obstructing his vision. The diver's system includes a microprocessor, and has an input capability that allows a diver to select one or more dive parameters before a dive. A plurality of sensors, connected to the microprocessor, are provided to monitor parameters such as air tank pressure, depth and water temperature. The system monitors these parameters during the ensuing dive, and provides warnings upon any of a variety of conditions occurring, such as if one or more of the parameters are violated. Throughout the dive, the system periodically stores dive data and any warnings (if present) in a static RAM. Subsequent to the dive, the stored information can be downloaded into an external computer through a provided external port. The display system of the preferred embodiment includes an LED display that is reflected from a red reflecting mirror affixed to the diver's face mask so that the image of the LEDs is positioned well within the diver's line of sight, but appears to be at a comfortable viewing distance from the diver's eyes, this distance being greater than the distance from the eyes to the mirror. Thus, simply by looking through his face mask, the diver can continuously monitor a display of pertinent dive information such as depth and water temperature, as well as essential information such as air tank pressure. This system is described in great detail in the Barr patent, and the same basic system including the arrangement, circuitry, display elements, alarms, and memory for storing information, can be easily adapted to the present invention for providing a heads-up display in surgical eyewear or a surgical loupe. Thus, the teachings of this patent are expressly incorporated herein by reference.

The heads up display may also be a more elaborate system as described in U.S. Pat. No. 5,343,313 (Fergason) which includes, in addition to the heads up display, a system for protecting the eyes of a wearer from high intensity electromagnetic radiation such as laser energy. However, in the surgical environment a surgeon will maintain control over the laser emission and thus a complex device for protecting the eyes from accidental laser irradiation is not required nor desired.

Specific controls and displays useful for laser surgery according to the present invention will now be discussed in greater detail by reference to the drawings.

Medical Laser System

The laser system modified in accordance with the present invention may be any medical laser, since these are not currently provided with surgeon fingertip control. Lasers may be used for surgical applications requiring ablation, vaporization, excision, incision, and coagulation of soft tissue in medical specialties including dermatology, plastic surgery, podiatry, neurosurgery, gynecology, otorhinolaryngology (ENT), arthroscopy (knee surgery), and envasive and endoscopic general surgery. Examples of such medical laser systems are disclosed in the following Table:

TABLE 1

U.S. Pat. No. 5,644,585 High repetition rate Erbium-YAG laser for tissue ablation U.S. Pat. No. 5,642,370 High repetition rate Erbium-YAG laser for tissue ablation U.S. Pat. No. 5,634,737 Coupler for attaching an articulated arm to a laser U.S. Pat. No. 5,578,029 Method of treating veins U.S. Pat. No. 5,558,667 Method and apparatus for treating vascular lesions U.S. Pat. No. 5,558,666 Handpiece for producing highly collimated laser beam for dermatological procedures U.S. Pat. No. 5,454,808 Surgical laser handpiece for slit incisions U.S. Pat. No. 5,360,447 Laser assisted hair transplant method U.S. Pat. No. 5,312,398 Apparatus for delivering a laser beam U.S. Pat. No. 5,304,174 Micromanipulator apparatus for surgical laser U.S. Pat. No. 5,254,114 Medical laser delivery system with internally reflecting probe and method U.S. Pat. No. 5,171,242 Combination lens system for retinal photocoagulator laser system U.S. Pat. No. 5,170,409 Laser resonator assembly U.S. Pat. No. 5,166,513 Dual actuation photoelectric foot switch U.S. Pat. No. 5,136,676 Coupler for a laser delivery system U.S. Pat. No. 5,131,004 RF excited $CO_2$ slab waveguide laser U.S. Pat. No. 5,037,421 Mid-infrared laser arthroscopic procedure U.S. Pat. No. 4,862,886 Laser angeoplasty U.S. Pat. No. 4,707,837 Distributive lasing system Further detailed information can be found in the following operating manuals published by Coherent, Inc., of Palo Alto, Calif.: "True Spot™ Collimated Handpieces—Carbon Dioxide Laser Delivery System"; "0.2 Millimeter and 1.0 Millimeter Handpieces—Carbon Dioxide Laser Delivery Systems"; "Ultrascan™ Computer Pattern Generator Carbon Dioxide Laser System"; and "UltraPulse™ Carbon Dioxide Surgical Lasers Operator Manual".

Figure 7:
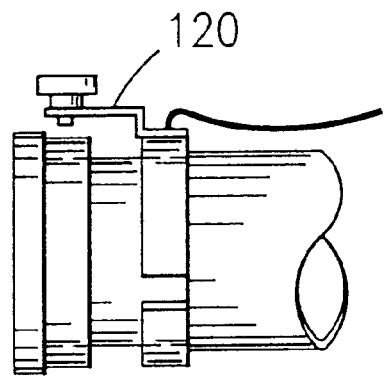
FIG. 7 shows a side view of the simple metal leaf spring of FIG. 2.
Figure 8:
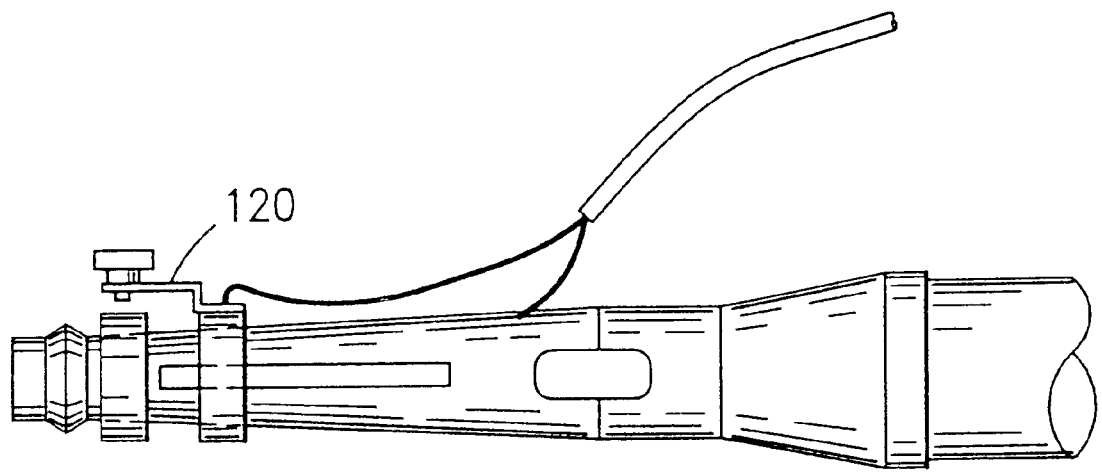
FIG. 8 shows a CW laser modified according to the present invention.
Figure 9:
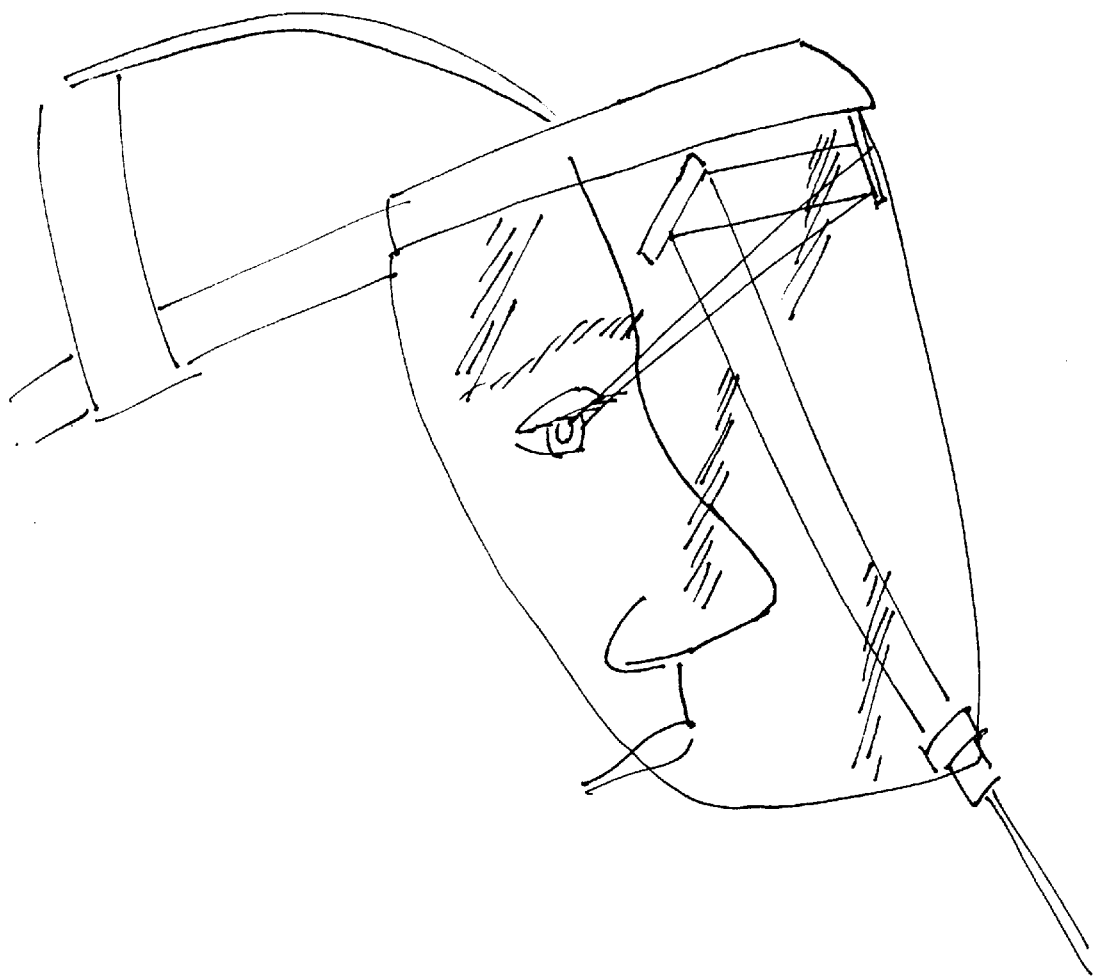
FIG. 9 shows the remote operator interface console display as a heads-up display provided in eyewear for wearing by a surgeon.

As shown in FIG. 1, the standard laser system 1 which is easily modified in accordance with the present invention comprises a footpedal receptacle 2, footpedal cable receptacle 3, CRT or video status or control display screen 4, mast 5, mast display 6, and laser system articulated arm 7 terminating in a computer pattern generator (CPG) (see FIG. 2) or continuous wave (CW) laser (see FIG. 7) handpiece receptacle 8. To the extent that the laser system is shown in FIG. 1, the system is standard and unmodified.

Figure 2:
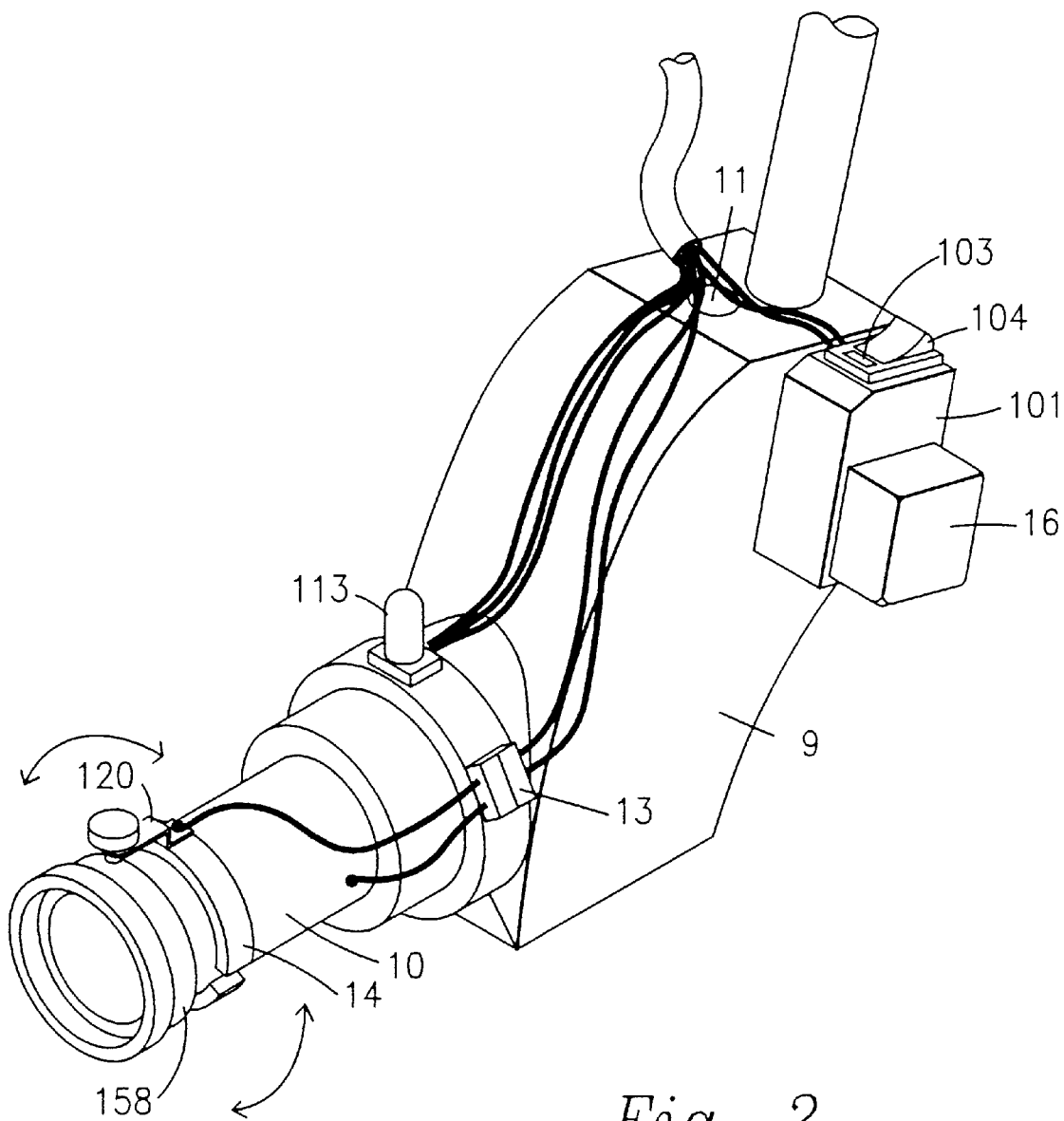
FIG. 2 shows a combination CPG and handpiece modified in accordance with the present invention.
Figure 5:
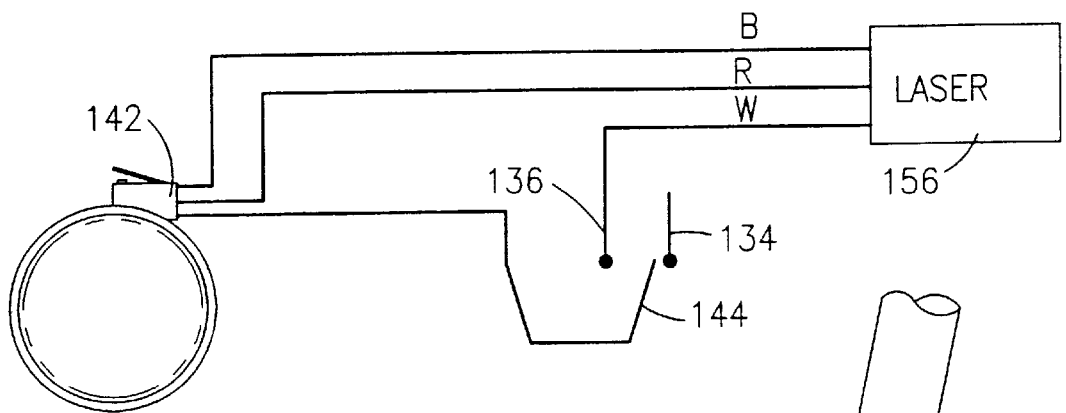
FIG. 5 shows a basic wiring schematic for a simple handpiece modification according to the invention.

Modifications are shown in FIG. 2. CPG unit 9 is connected to the distal end 8 of articulated arm 7, and handpiece 10 is attached to the CPG unit 9. CPG unit 9 receives input from the main console via a cable (not shown) which is received in receptacle 11. The most significant modification to the laser system comprises a switch which may be a leaf switch 120 as in FIG. 2 or a microswitch 142 as shown in FIG. 5 for activation of the laser 156. As shown in FIG. 2, the leaf switch 120 is connected to a wire which constitutes part of a circuit. Leaf switch 120 is mounted in a plastic ring 121 which is an insulator and which is free to rotate about handpiece 10. At the distal end of the handpiece is a metal ring 158 such as an aluminum ring. Metal ring 158 is mounted on and contacts metal handpiece 10. A second wire of the same circuit mentioned above is attached to the metal handpiece 10. Depressing leaf spring switch 120 closes the electrical circuit from the first wire, through the metal leaf spring 120, through the metal ring 158, through metal handpiece 10, and through the second wire. The advantage of mounting the leaf spring 120 on plastic ring 121 is that this allows the surgeon to rotate the switch 120 for greatest comfort depending on the orientation of the handpiece (normal, tilted, upside down, etc.) and depending upon whether the surgeon is holding the laser with the left hand or the right hand. As shown in FIG. 2, leaf spring 120 can be easily detached from CPG 9 via electrical connector 13.

Considering next the microswitch of FIG. 5, electronically the microswitch 142 is identical to a switch located in a foot pedal. The microswitch 142 of the present invention is, however, located at the distal end of the handpiece 10, in the area where a fingertip of the surgeon is normally located during surgery. Instead of the standard footpedal cable, the present invention employs a microswitch wire harness which is routed on or through the handpiece 10, CPG 9, and along the laser system articulated arm 7. In a basic and unmodified system, this laser activation wire harness may be plugged directly into the "footpedal" cable receptacle 3.

The remote laser control system according to the present invention in an elementary form functions simply to turn the laser on and off. In order to control the laser three wires are required, which in FIG. 5 are labeled R, B and W for red, black and white. When microswitch 142 is in the raised or "off" position, the black B and the red R wire circuit will be closed, this circuit telling the laser to be off. When the microswitch 142 is depressed, it will close the black B and white W circuit, telling the laser to fire.

For improved safety, interrupt or safety switch 144 may be provided on the handpiece held by the surgeon. When switch 144 contacts terminal 134 in the position shown in FIG. 5, depressing microswitch 142 will not complete the black-white circuit, thus switch 144, when in the open or "standby" position, prevents the laser from firing. When switch 144 contacts terminal 136, switch 144 is in the "ready" position and the black-white circuit can be closed upon depressing microswitch 142. The switch 144 may be a spring biased switch which requires constant pressure to remain in the "on" position (thereby ensuring two-handed operation of the laser), but is more preferably a flip switch which can be flipped between an "on" and an "off" position so that the surgeon is free to use his second hand for other tasks such as stretching skin or operating the remote console.

Laser Standby/Ready Switch

The power supply and control circuits, which are conventionally connected to the output of a foot switch, are herein connected to a finger operated microswitch (either directly or via a solenoid). The CPG is provided not only with an on/off switch, but also with a ready/standby switch which is set to "ready" as a conventional safety measure. When the surgeon has completed his surgical procedure, the technician operating the control panels is supposed to flip the laser "ready/standby" switch into standby mode. In the present invention the need to have a technician operating the control panel is completely or nearly completely eliminated.

Figure 6:
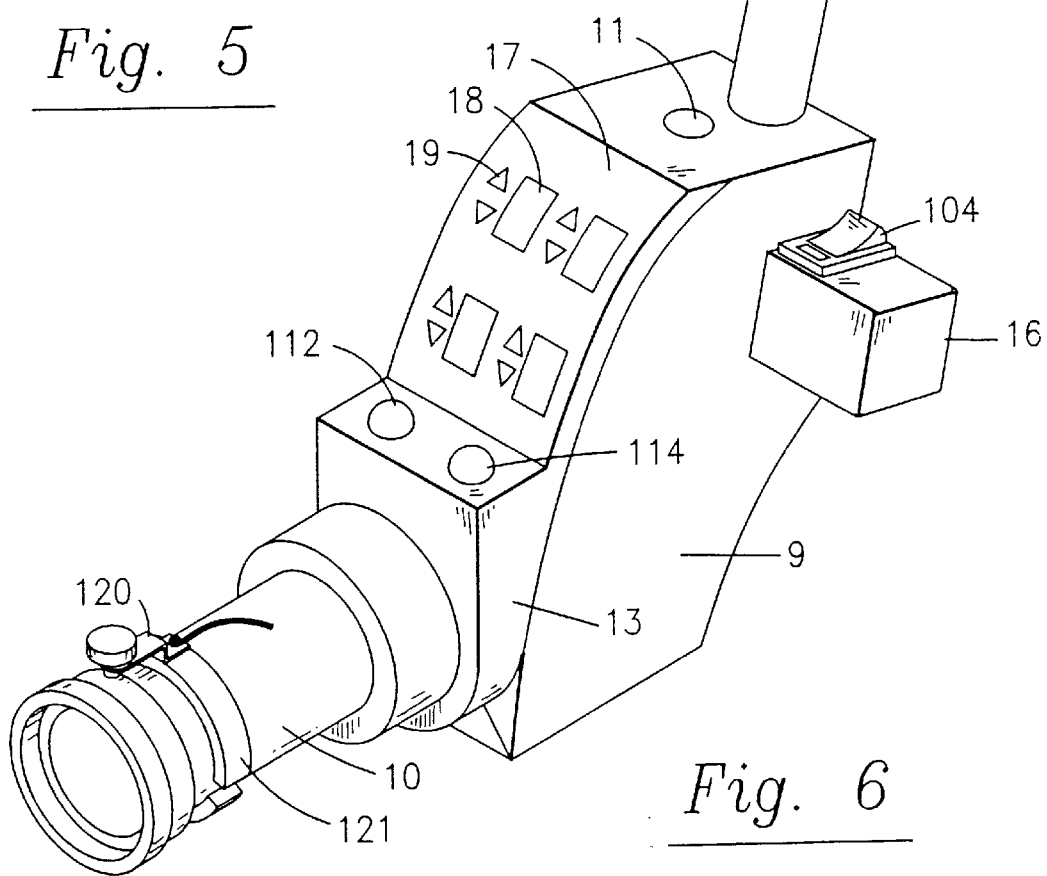
FIG. 6 shows a laser handpiece with remote controls and miniature remote display according to the invention.

The present inventor considered that the CPG 9 is provided with a handpiece 10 for gripping with one hand and a small handle or projection 16 for gripping with the second hand. That is, in practice the surgeon requires only one hand to operate the conventional CPG, thus leaving the second hand idle. The CPG is provided with a small handle 16 which is designed to be grasped by one hand as the other hand grasps the handpiece 10. In the present invention, in order to eliminate the need to have the laser operator operate the "standby/ready" switch from the main console, the CPG unit 9 may be provided with a "standby/ready" switch 104. This switch may be provided anywhere on the CPG 9 or handpiece 10, but is preferably ergonomically provided on the small handle 16 which is designed to be grasped by the surgeon during operation, the switch either being provided as a retrofit item such as a rubber unit 101 which can be slid onto the small handle 16 as shown in FIG. 2, or may be built into the handle 16 as original equipment as shown in FIG. 6. The switch is designed so that as the second hand grasps the CPG handpiece, it conveniently and almost automatically activates the "ready" switch and places the laser in the ready mode. The switch may be a spring biased switch which requires constant pressure to remain in the "on" position, but is more preferably a flip switch which can be flipped between an "on" and an "off" position. This way the surgeon is free to use his second hand for other tasks such as stretching skin or operating the remote console.

Figure 4:
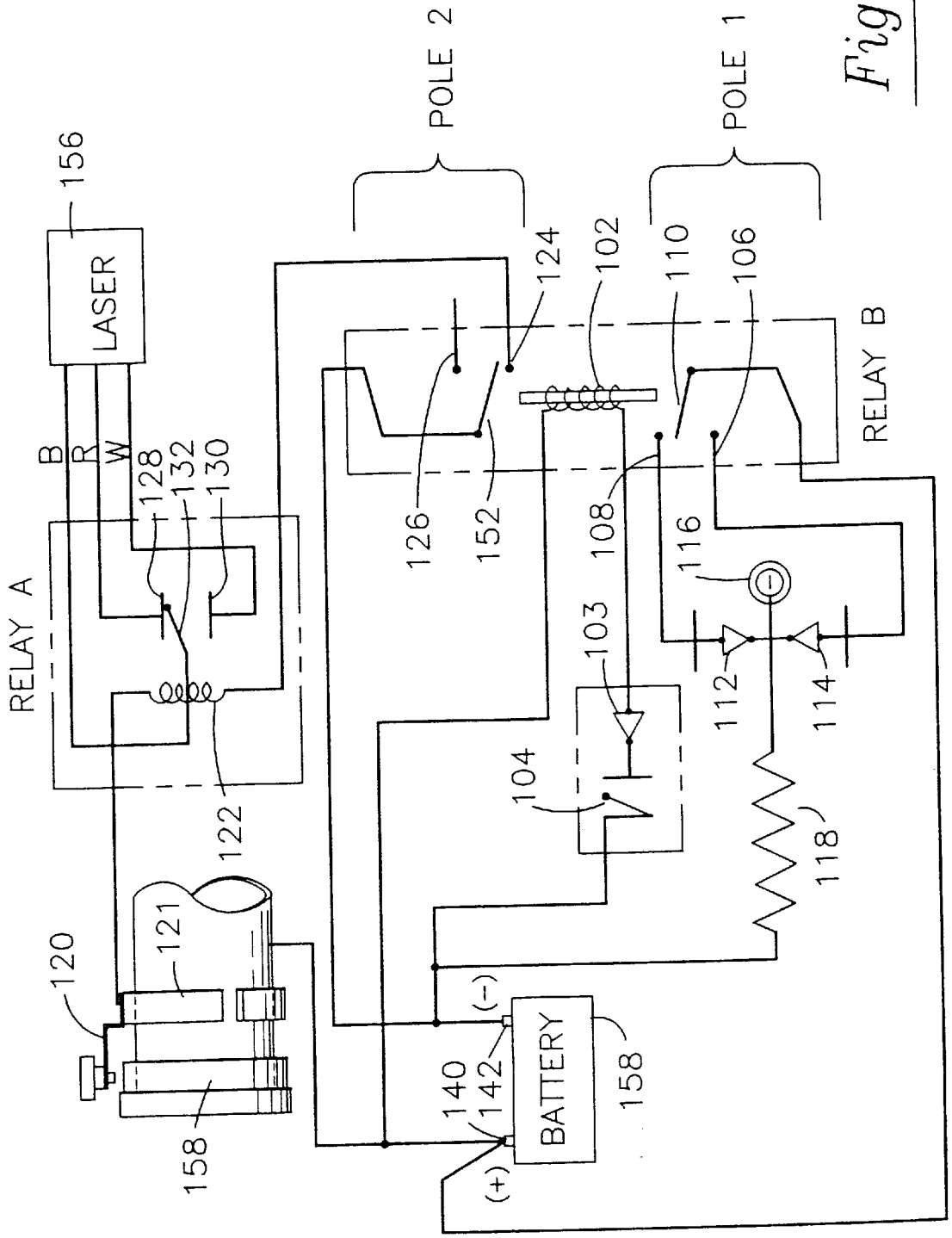
FIG. 4 shows the wiring schematic for the modified handpiece shown in FIG. 2.

Turning to FIG. 4, this figure illustrates the circuitry of the embodiment shown in FIG. 2. The Relay B in FIG. 4 is a two-pole relay unit. Pole 1 is associated with LED display 112 and 114. Pole 2 is a switch that will act as a safety to interrupt the coil found in Relay A circuit and thereby interrupting the circuit containing the hand switch 120 at the laser hand piece, disenabling it from firing. In the upper half of FIG. 4 this illustrates Relay A directly controlling the laser 156 through wires B, R and W. The switch 120 at the laser handpiece activates and deactivates the coil 122 in Relay A in order to control the three wire output (B, R and W) of Relay A which is directly controlling the laser. It's operational status is dependent upon the switch 152 at pole 2, which in turn is controlled by switch 104. When ready/standby switch 104 is in the ready position as shown in FIG. 4, it closes an electrical circuit through coil 102 thereby activating coil 102. This causes switch 152 to move towards coil 102, such that switch 152 contacts terminal 124 and so that there is no interruption of the circuit controlled by switch 120 at this point. This makes it possible to close the coil circuit in Relay A by moving metal leaf spring switch 120 downwards such that the switch 120 contacts aluminum ring 158. Aluminum ring 158 is electrically conductive and completes the coil circuit of Relay A. Completing the coil circuit of Relay A energizes coil 122 which causes switch 132 to move from red wire R terminal 128 to white wire W terminal 130, closing the circuit which causes the laser 156 to fire. On the other hand, when switch 152 is in the open position (not shown in FIG. 4), this causes an interrupt of the coil circuit of Relay A.

In the course of working with a laser there are times when the surgeon believes the laser to be in the ready mode and tries to fire the laser, only to discover that the laser is in the standby position. It also happens that the surgeon believes the laser to be in the standby position and accidentally activates the laser trigger, causing the laser to fire. To prevent such problems, the laser handpiece in accordance with the present invention is provided with LED displays to signal the status of the laser. These displays are shown in FIG. 2 and the associated circuitry is shown in the lower half of FIG. 4, In FIG. 4 when the safety switch 104 is activated it completes the circuit through power source 158 and through a green LED 103 back through the switch 104, the circuit being activated and green LED fluorescing. When the ready/standby circuit is completed from positive terminal 140 of power source 158 going through the coil 102 in the Relay B then through the green led 103 through the switch 104 back to the negative terminal 142 of the power supply 158, coil 102 causes switch 110 to flip from terminal 106 to terminal 108. When looking at Pole 1 of Relay B, in the case that ready/standby switch 104 is in the standby (off) position, switch 110 is connected to terminal 106 completing the circuit going from the battery through switch 110, through terminal 106, through the red led at 114, through the resistor 118 back to the power supply negative terminal at 142. This would indicate that all of the circuits are in the off position and are deactivated. When the ready/standby switch at 104 is active it activates the coil at 102 thereby switching switch 110 from terminal 106 to terminal 108, completing the circuit from the power supply positive terminal 140 through switch 110, through terminal 108, through green LED 112, through resistor 118 and back to the negative terminal 142 of the power supply 158. Green LED 112 being illuminated thus also shows that the coil circuit Relay A is in the ready position since Relay A is in the ready position with switch 152 contacting terminal 124. Accordingly, with green LED 112 illuminated (and green LED 103 illuminated), switch 120 is enabled and the laser can be fired by contacting switch 120 to aluminum ring 158, thus completeing the coil circuit of relay thus activating the switch 132 from 128 to 130 thus completing the B-W circuit and thus firing the laser.

Laser On/Off (Activation) Switch

The present invention differs from the prior art primarily in the placement of the laser activation switch. This modification is believed to comply with FDA/CDRH Federal Laser Product Performance Standard and the general laser product safety standards requirements of 21 CFR Subchapter J. including Part 1040.10 and 1040.11; IEC 825-2; EN 60825-1; and EN 60825-1.

As discussed above, the switch is preferably a microswitch designed to alternatively close an "on" circuit and an "off" circuit. Pressing the microswitch closes an "on" circuit and causes activation of the laser (as long as the laser is already in the "ready" mode), and releasing the switch causes the microswitch to flip back and close an "off" circuit, sending a deactivation signal to the laser. Besides size and placement, this switch function and logic are identical to the standard foot pedal switch.

As an alternative to the dual circuit three-wire microswitch, the switch may be a simple contact switch such as a membrane switch which is connected to a solenoid, which solenoid is designed to operate a laser activation switch switching between an "on" circuit and an "off" circuit.

Since the surgeon's hand may grasp the CPG handpiece at various orientations, the microswitch is preferably mounted in a manner so that it can be easily repositioned, such as being provided on a plastic annular ring which circumscribes the distal end of the handpiece. The microswitch may be connected to the wiring harness of the articulated arm either via an extra length of wire, or via slip ring contacts.

Laser Control Remote Console

A laser remote control console can be a separate unit from the controls provided on the CPG handpiece, and can take the form of the remote console as provided in U.S. Pat. No. 5,249,121 (Baum et al). In a more preferred embodiment at least some of the main controls are either built directly into the laser CPG handpiece housing or are provided on a shell or overlay which is adapted to fit flush against and attach directly to the CPG handpiece. This control module contains one or more control switches for controlling one or more of the following functions (given in order of preference):

- laser ready and laser standby
- density
- pattern (1–79)
- size
- energy (millijoules)
- rate
- power (watts)

Structurally the remote controller may be comprised of: communication means, connected to the main processor for allowing the control system to communicate information to the remote controller that is to be displayed, and for transmitting to the main processor information entered by a user at the remote controller. The remote controller may further comprise input means for enabling the user of the remote controller to enter information to be received by the main processor, and light emitting means, connected to the commutation means, for emitting light therefrom in response to communicated information that is to be displayed. The remote controller further preferably utilizes a plurality of membrane switches or other types of switches arranged in a predetermined pattern which emulates at least part of the pattern in which the operator input switches on the main console are arranged.

As described in U.S. Pat. No. 5,033,818 (Barr) incorporated herein by reference, an oscillator may provide the internal clocking necessary for operation of a microcontroller (MCU). A reset circuit may be connected to the MCU to reset the MCU to a known state after power-up of the system. A plurality of switches are connected to the MCU so that the surgeon may provide inputs to the MCU for selection purposes. A connector is connected to the microcontroller to provide an interface (such as the well known RS232 interface) with an external PC terminal for purposes such as downloading of data.

Located in the display section is an anode driver for specifying the digit segments of an LED display and a shift register for digit selection. The shift register is comprised of components which drive the cathodes of the LED segments as will be later described. Both the anode driver and the shift register are connected to the MCU. Furthermore, both the anode driver and the shift register are connected to the LED display which may, for example, be mounted in or on the laser CPG handpiece or within the eyewear of the surgeon using the present invention.

In the embodiment shown in FIG. 2, the CPG is provided with a mini-console 17 with LED indicators 18 and membrane switches 19 for controlling the settings. The frequently used functions, such as density, pattern, size and energy may be controlled via this remote console 17, which repeats certain of the functionalities of the main console as shown in FIG. 3. The console 17 may be added to the CPG unit as an after market item, in which case the surgeon may mount the unit on either the left side or the right side of the CPG unit 9, depending upon whether the surgeon is left handed or right handed. The mini-console 17 may be connected to the main console in any of a variety of ways as discussed above.

Memory

In order to provide extended storage facilities and to provide additional programming for the MCU in the preferred embodiment, the MCU is preferably connected to a memory section as described in detail in U.S. Pat. No. 5,033,808 (Barr). Within this memory section, an address latch is connected to the MCU. The address latch is also connected to a multiplexer to access the particular memory device selected by the MCU. One of these memory devices is a UV erasable programmable read-only memory (EPROM) which is connected to the multiplexer and a non-volatile storage random access memory (RAM) also connected to the multiplexer. Additionally, the address latch is connected to the EPROM and the storage RAM in order to address the respective location within either of the memory devices. Furthermore, the storage RAM is connected to the microcontroller to provide read and write capabilities. It will be appreciated by those skilled in the art that additional memory configurations or differing components may be substituted to provide the desired additional memory or storage capabilities.

Heads-up Display

The surgeon's eyewear generally forms an enclosure with a lower surface, an upper surface, and a front transparent surface. The display may include an LED display box housed in a lower portion, with the displayed digits facing the top of the eyewear. The top of the eyewear includes a mirror for reflecting light from the LEDs to the front transparent surface which in this display system is partially silvered.

The optical path from the display to the eyes of the surgeon begins at the display, which is housed in the lower portion and extends upward to the mirror. The light is reflected by the mirror toward the eyewear transparent surface, which supports a partially reflecting mirror. The partially reflecting mirror reflects the light along the optical path toward the eyes of the surgeon and terminates in the eyes. The total length of the optical path is sufficient to permit easy viewing of the "virtual image" by the surgeon.

Speech Recognition and Spoken Alarms

Speech recognition programs are well known and any of a variety of programs can easily be adapted for use with the present invention. An example of such a system is the speech controlled vehicle alarm system as disclosed in U.S. Pat. No. 5,706,399 (Bareis). This system allows control of alarm functions to be accomplished using specific spoken commands. A microphone converts speech into time variant voltage levels which are amplified and sent to an analog-to-digital converter and digitized. The digitized data is then processed by a speech recognition subsystem. The speech recognition subsystem separates extraneous speech from words (commands) and provides corresponding output signals when control words are recognized. While the output signals are used in this patent to operate door locking and unlocking controls, to operate a loud siren, to operate vehicle light controls, to provide an engine cut-off control, to provide an engine starting control, or to operate a response indicator incorporated in the main alarm processing unit, it will be easily appreciated that the same system may be used in the operating room to control laser beam CPG pattern selection, pattern width, beam intensity, or to respond to spoken status inquiries. Response to spoken inquiries may be by either presenting an updated or selected visual display, or by providing a spoken status. Spoken status or alarms may be provided by pre-programmed microchips, or for greater flexibility may be provided by a computer program including a speaking program. Examples of such computer programs include "VoiceType™ Simply Speaking" by IBM and "Power Translator®" by Globalink. Further examples of voice recognitions include U.S. Pat. No. 5,664,061 (Andreshak, et. al.) teaching an interactive computer system recognizing spoken commands.

As to the manner of usage and operation of the two embodiments of the present invention described above, the same should be apparent from the above description.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Now that the invention has been described,

What is claimed is:

1. A medical laser system comprising:
   a laser rod for generating a treatment beam;
   a laser housing for housing said laser rod;
   an articulated arm having a proximal end and a distal end, the proximal end of which is connected to said laser housing, through which articulated arm said treatment beam is guided;
   a handpiece designed to be held by a surgeon and having a proximal end and a distal end, the handpiece proximal end connected to the articulated arm distal end, such that said treatment beam exits through said handpiece distal end; and
   a switch means located at said handpiece generating a control signal for initiating delivery of said treatment beam.

2. A medical laser system as in claim 1, wherein said handpiece is provided with a standby/ready switch to generate a control signal such that when said standby/ready switch is in the standby position said switch means is disabled from initiating delivery of said treatment beam, and when said standby/ready switch is in the ready position said switch means is enabled to initiate delivery of said treatment beam.

3. A medical laser system as in claim 1, wherein said handpiece includes a computer pattern generator.

4. A medical laser system as in claim 1, wherein said handpiece includes a LED which is illuminated when said laser is in the ready state.

5. A medical laser system as in claim 4, wherein said LED emits green light.

6. A medical laser system as in claim 1, wherein said handpiece includes a LED which is illuminated when said laser is in the standby state.

7. A medical laser system as in claim 6, wherein said LED emits red light.

8. A medical laser system as in claim 1, wherein said laser activation switch is a microswitch.

9. A medical laser system as in claim 1, wherein said laser activation switch is a metal leaf spring switch.

10. A medical laser system as in claim 1, wherein said laser activation switch closes a circuit which activates a coil which activates a laser control switch.

11. A medical laser system as in claim 1, wherein said laser system includes a main operator interface console for controlling a plurality of laser system functions and a remote operator interface console for controlling a plurality of laser system functions.

12. A medical laser system as in claim 11, wherein one of said main operator interface console and remote operator interface console are controlled via voice recognition.

13. A medical laser system as in claim 1, wherein said laser system includes a main operator interface console display for displaying the status of a plurality of laser system functions and a remote operator interface console display for displaying the status of a plurality of laser system functions.

14. A medical laser system comprising:
   a laser rod for generating a treatment beam;
   a laser housing for housing said laser rod;
   an articulated arm having a proximal end and a distal end, the proximal end of which is connected to said laser housing, through which articulated arm said treatment beam is guided;
   a handpiece designed to be held by a surgeon and having a proximal end and a distal end, the handpiece proximal end connected to the articulated arm distal end, such that said treatment beam exits through said handpiece distal end; and
   a switch means located at said handpiece generating a control signal for initiating delivery of said treatment beam,
   wherein said laser system includes a main operator interface console display for displaying the status of a plurality of laser system functions and a remote operator interface console display for displaying the status of a plurality of laser system functions, and
   wherein said a remote operator interface console display is provided on said handpiece designed to be held by a surgeon.

15. A medical laser system comprising:
   a laser rod for generating a treatment beam;
   a laser housing for housing said laser rod;
   an articulated arm having a proximal end and a distal end, the proximal end of which is connected to said laser housing, through which articulated arm said treatment beam is guided;
   a handpiece designed to be held by a surgeon and having a proximal end and a distal end, the handpiece proximal end connected to the articulated arm distal end, such that said treatment beam exits through said handpiece distal end; and
   a switch means located at said handpiece generating a control signal for initiating delivery of said treatment beam,
   wherein said laser system includes a main operator interface console display for displaying the status of a plurality of laser system functions and a remote operator interface console display for displaying the status of a plurality of laser system functions, and
   wherein said a remote operator interface console display is a heads-up display provided in eyewear for wearing by a surgeon.

16. A medical laser system comprising:
   a laser rod for generating a treatment beam;
   a laser housing for housing said laser rod;
   an articulated arm having a proximal end and a distal end, the proximal end of which is connected to said laser housing, through which articulated arm said treatment beam is guided;

a handpiece designed to be held by a surgeon and having a proximal end and a distal end, the proximal end connected to the distal end of said articulated arm, such that said treatment beam exits through said handpiece distal end;

a switch means located at said handpiece generating a control signal for initiating delivery of said treatment beam; and a remote operator interface console for controlling a plurality of laser system functions, said system having a main control console, said main control console having a main processor and a display screen for simultaneously displaying multiple fields of information associated with the laser system, the remote console comprising:

communications means, connected to the main processor, for causing the remote console to communicate laser system operating function data with the control system; and remote display means, connected to the communication means, for simulating the display of at least part of the fields of information associated with the laser system displayed on the main console display screen, the remote display means selectably activated by data transmitted from the main control console; and microcontroller means, connected to the light emitting means, for receiving the transmitted data and activating individual ones of the light emitting means in response thereto.

17. A medical laser system as in claim 16, wherein said remote display means includes a plurality of light emitting means.

18. A medical laser system as in claim 16, wherein said remote display means includes a plurality of liquid crystal display means.

* * * * *